(12) United States Patent
Wen

(10) Patent No.: US 9,746,833 B2
(45) Date of Patent: Aug. 29, 2017

(54) ELECTRONIC DEVICE AND SMART METHOD FOR CONTROLLING ALARM

(71) Applicants: Fu Tai Hua Industry (Shenzhen) Co., Ltd., Shenzhen (CN); HON HAI PRECISION INDUSTRY CO., LTD., New Taipei (TW)

(72) Inventor: Jun Wen, Shenzhen (CN)

(73) Assignees: Fu Tai Hua Industry (Shenzhen) Co., Ltd., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 51 days.

(21) Appl. No.: 14/735,723

(22) Filed: Jun. 10, 2015

(65) Prior Publication Data
US 2016/0202667 A1    Jul. 14, 2016

(30) Foreign Application Priority Data
Jan. 8, 2015   (CN) .......................... 2015 1 0009531

(51) Int. Cl.
| | | |
|---|---|---|
| G08B 29/00 | (2006.01) |
| G04G 13/02 | (2006.01) |
| A61B 5/00 | (2006.01) |
| A61B 5/08 | (2006.01) |
| A61B 7/00 | (2006.01) |
| A61B 5/0402 | (2006.01) |
| A61B 5/0476 | (2006.01) |
| A61B 5/0245 | (2006.01) |

(52) U.S. Cl.
CPC .......... *G04G 13/02* (2013.01); *A61B 5/4809* (2013.01); *A61B 5/0245* (2013.01); *A61B 5/0402* (2013.01); *A61B 5/0476* (2013.01); *A61B 5/0816* (2013.01); *A61B 5/6891* (2013.01); *A61B 7/003* (2013.01)

(58) Field of Classification Search
CPC ... A61B 5/0245; A61B 5/0402; A61B 5/0476; A61B 5/0816; A61B 5/4809; A61B 5/6891; A61B 7/003; G04G 13/02
USPC .......................................... 340/506; 368/73
See application file for complete search history.

(56) References Cited

U.S. PATENT DOCUMENTS

2014/0269223 A1* 9/2014 Mokhnatkina ......... G04G 13/02
368/73

* cited by examiner

*Primary Examiner* — Ojiako Nwugo
(74) *Attorney, Agent, or Firm* — Steven Reiss

(57) ABSTRACT

An electronic device and a smart method for controlling an alarm are provided. The smart method includes, controlling a collection device to collect physiological parameters of a user when an alarm device of the electronic device sounds an alarm at a schedules time, obtaining the physiological parameters collected by the collection device, and determining whether the user is asleep or awake according to the obtained physiological parameters. The alarm device is disabled if the user is awake.

3 Claims, 2 Drawing Sheets

ELECTRONIC DEVICE AND SMART METHOD FOR CONTROLLING ALARM

CROSS-REFERENCE TO RELATED APPLICATIONS

This application claims priority to Chinese Patent Application No. 201510009531.1 filed on Jan. 8, 2015, the contents of which are incorporated by reference herein.

FIELD

The subject matter herein generally relates to an electronic device and a smart method for controlling an alarm of the electronic device.

BACKGROUND

An alarm of an alarm clock will repeat every few minutes if it is not turned off.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

Figure 1:
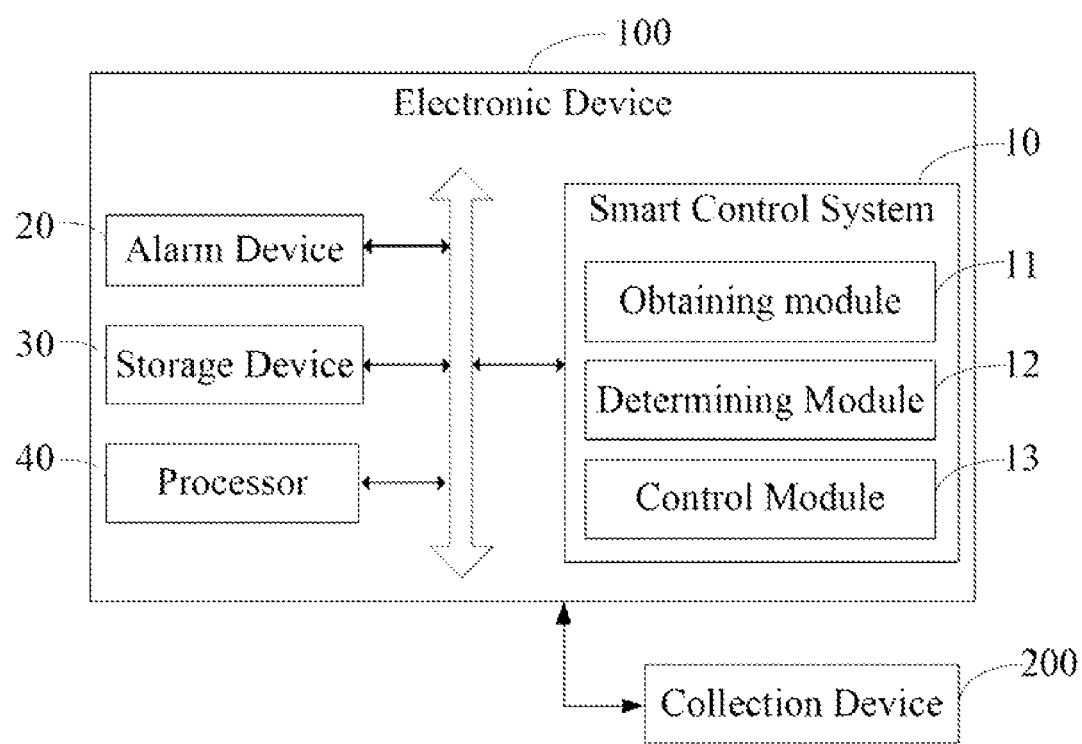
FIG. 1 is a block diagram of an embodiment of an electronic device including a smart alarm control system.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in details so as not to be considered as limiting the scope of the embodiments described herein. The drawings are not necessarily to scale and the proportions of certain parts may be exaggerated to better illustrate details and features of the present disclosure.

The present disclosure, including the accompanying drawings, is illustrated by way of examples and not by way of limitation. Several definitions that apply throughout this disclosure will now be presented. It should be noted that references to "an" or "one" embodiment in this disclosure are not necessarily to the same embodiment, and such references mean "at least one".

Furthermore, the term "module", as used herein, refers to logic embodied in hardware or firmware, or to a collection of software instructions, written in a programming language, such as Java, C, or assembly. One or more software instructions in the modules can be embedded in firmware, such as in an EPROM. The modules described herein can be implemented as either software and/or hardware modules and can be stored in any type of non-transitory computer-readable medium or other storage device. Some non-limiting examples of non-transitory computer-readable media includes CDs, DVDs, BLU-RAY, flash memory, and hard disk drives. The term "comprising" means "including, but not necessarily limited to"; it specifically indicates open-ended inclusion or membership in a so-described combination, group, series and the like.

FIG. 1 illustrates a block diagram of an embodiment of an electronic device. In at least one embodiment as shown in FIG. 1, an electronic device 100 includes, but is not limited to, a smart control system 10, an alarm device 20, a storage device 30 and at least one processor 40. The electronic device 100 can be a tablet computer, a notebook computer, a smart phone, a personal digital assistant (PDA), or another suitable electronic device. FIG. 1 illustrates only one example of the electronic device 100 that can include more or fewer components than illustrated, or have a different configuration of the various components in other embodiments.

The alarm device 20 can sound alarm at a scheduled time. In the embodiment, the alarm device 20 is an alarm clock. In at least one embodiment, the storage device 30 can include various types of non-transitory computer-readable storage mediums. For example, the storage device 30 can be an internal storage system, such as a flash memory, a random access memory (RAM) for temporary storage of information, and/or a read-only memory (ROM) for permanent storage of information. The storage device 30 can also be an external system, such as a hard disk, a storage card, or a data storage medium. The at least one processor 40 can be a central processing unit (CPU), a microprocessor, or other data processor chip that performs functions of the smart control system 10 in the electronic device 100.

In some embodiments, a collection device 200 is connected to the electronic device 100, and the collection device 200 can collect physiological parameters, such as breathing rate, muscle fatigue, brain waves and heart rate. The collection device 200 can be breathing sound sensor, smart bracelet, electroencephalograph (EEG) sensor, electrocardiogram (ECG) sensor and the like. The collection device 200 can be an independent device, or be built into the electronic device 100.

The smart control system 10 can determine whether a user is asleep or awake according to physiological parameters collected by the collection device 200, and disable the alarm device 20 if the user is awake.

In at least one embodiment, the smart control system 10 can include an obtaining module 11, a determining module 12 and a control module 13. The function modules 11-13 can include computerized codes in the form of one or more programs, which are stored in the storage device 30. The at least one processor 40 executes the computerized codes to provide functions of the function modules 11-13.

The control module 13 controls the collection device 200 to collect physiological parameters of a user when the alarm device 20 sounds an alarm at the scheduled time.

The obtaining module 11 obtains the physiological parameters collected by the collection device 200.

The determining module 12 determines whether the user is asleep or awake according to the obtained physiological parameters.

In some embodiments, the storage device 30 stores physiological parameter ranges of a user asleep. The determining module 12 compares the obtained physiological parameters to the physiological parameter ranges to determine whether the user is asleep or awake. In at least one embodiment, if the obtained physiological parameters fall into the physiological parameter ranges, the determining module 12 determines the user is asleep; if the obtained physiological parameters do not fall into the physiological parameter ranges, the determining module 12 determines the user is awake.

In other embodiments, the storage device 30 stores physiological parameters of a user asleep and physiological parameters of the user awake. The determining module 12 compares the obtained physiological parameters to physiological parameters of the user asleep and physiological parameters of the user awake, to determine whether the user is asleep or awake. In at least one embodiment, if the obtained physiological parameters are closer to the physiological parameters of the user asleep, the determining module 12 determines the user is asleep; if the obtained physiological parameters are closer to the physiological parameters of the user awake, the determining module 12 determines the user is awake.

The control module 13 disables the alarm device 20 if the user is awake, and controls the alarm device 20 to sound alarm again few minutes after the scheduled time if the user is asleep.

Figure 2:
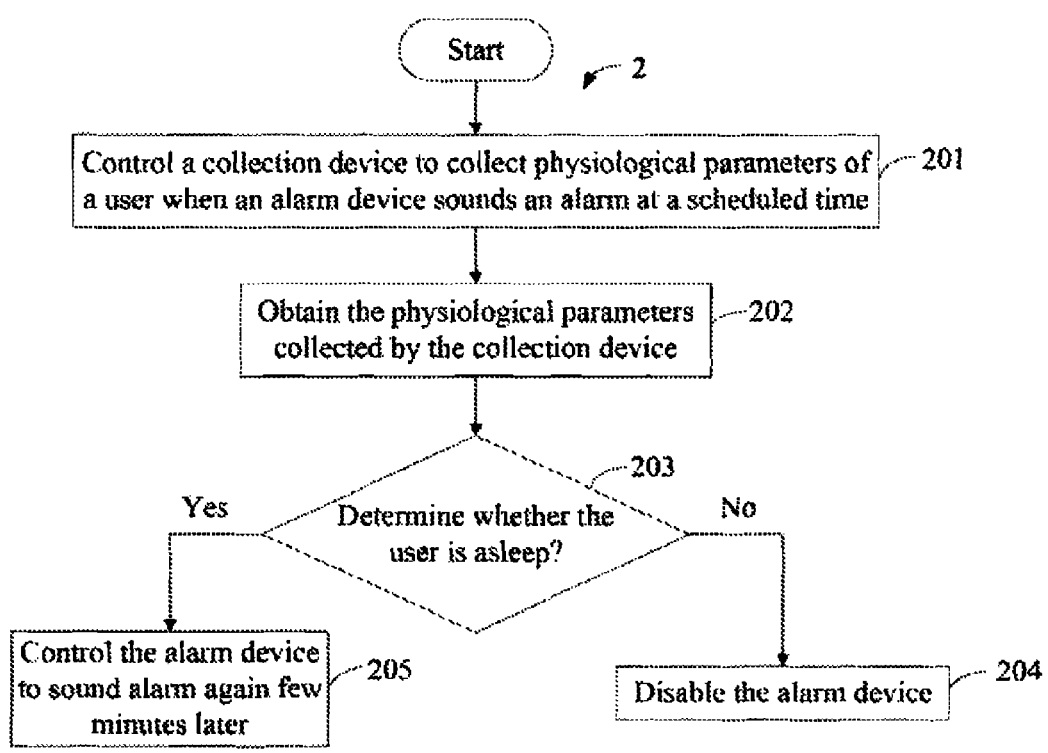
FIG. 2 illustrates a flowchart of an embodiment of a smart method for controlling alarm of the electronic device of FIG. 1.

Referring to FIG. 2, a flowchart of a smart method for controlling an alarm is presented in accordance with an example embodiment. The example method 2 is provided by way of example, as there are a variety of ways to carry out the method. The example method 2 described below can be carried out using the configurations illustrated in FIG. 1 for example, and various elements of these figures are referenced in explaining example method 2. Each block shown in FIG. 2 represents one or more processes, methods, or subroutines carried out in the example method 2. Furthermore, the illustrated order of blocks is by example only and the order of the blocks can be changed. The example method 2 can begin at block 201. Depending on the embodiment, additional steps can be added, others removed, and the ordering of the steps can be changed.

At block 201, a control module controls a collection device to collect physiological parameters of a user when an alarm device sounds an alarm at the scheduled time.

At block 202, an obtaining module obtains the physiological parameters collected by the collection device.

At block 203, a determining module determines whether the user is asleep or awake according to the obtained physiological parameters. If the user is asleep, block 205 is implemented; if the user is awake, block 204 is implemented.

At block 204, the control module disables the alarm device.

At block 205, the control module controls the alarm device to sound alarm again few minutes later.

With such a configuration, the alarm device can be disabled if the user is awake.

It should be emphasized that above-described embodiment of the present disclosure including any particular embodiments, are merely examples of implementations set forth for a clear understanding of the principles of the disclosure. Many variations and modifications can be made to the above-described embodiment(s) of the disclosure without departing substantially from the spirit and principles of the disclosure. All such modifications and variations are intended to be included herein within the scope of this disclosure and protected by the following claims.

What is claimed is:

1. An electronic device comprising:
   an alarm device;
   at least one processor coupled to the alarm device; and
   a non-transitory storage device that stores one or more programs which, when executed by the at least one processor, cause the at least one processor to:
      control a collection device to collect physiological parameters of a user when the alarm device sounds an alarm at a scheduled time;
      obtain the physiological parameters collected by the collection device;
      determine whether the user is asleep or awake according to the obtained physiological parameters; and
      disable the alarm device if the user is awake;
   wherein the physiological parameters comprise breathing rate, muscle fatigue, brain waves and heart rate.

2. A computer-implemented smart method for controlling alarm being executed by a processor of an electronic device, the method comprising:
   controlling a collection device to collect physiological parameters of a user when an alarm device of the electronic device sounds an alarm at a scheduled time;
   obtaining the physiological parameters collected by the collection device;
   determining whether the user is asleep or awake according to the obtained physiological parameters; and
   disabling the alarm device if the user is awake;
   wherein the physiological parameters comprise breathing rate, muscle fatigue, brain waves, and heart rate.

3. A non-transitory storage medium having stored thereon instructions that, when executed by a processor of an electronic device, causes the processor to perform a smart method for controlling alarm, the method comprising:
   controlling a collection device to collect physiological parameters of a user when an alarm device of the electronic device sounds an alarm at a scheduled time;
   obtaining the physiological parameters collected by the collection device;
   determining whether the user is asleep or awake according to the obtained physiological parameters; and
   disabling the alarm device if the user is awake;
   wherein the physiological parameters comprise breathing rate, muscle fatigue, brain waves, and heart rate.

* * * * *